United States Patent [19]

Langford et al.

[11] 4,066,589

[45] Jan. 3, 1978

[54] SOLVENT REPELLENT COMPLEXES

[75] Inventors: Nathaniel P. Langford, Somerset, Wis.; Edward W. Perrault, Roseville, Minn.

[73] Assignee: Minnesota Mining and Manufacturing Company, St. Paul, Minn.

[21] Appl. No.: 580,197

[22] Filed: May 23, 1975

[51] Int. Cl.$^2$ .............................................. C08L 33/02
[52] U.S. Cl. ......................... 260/29.6 H; 260/29.6 F; 260/29.6 HN; 260/29.6 RW; 260/29.6 Z; 260/29.6 N
[58] Field of Search .................... 260/29.6 H, 29.6 F, 260/29.6 HN, 29.6 RW, 29.6 Z, 29.6 N; 424/78

[56] References Cited

U.S. PATENT DOCUMENTS

| | | | |
|---|---|---|---|
| 3,100,180 | 8/1963 | Smith et al. | 260/29.6 F |
| 3,503,915 | 3/1970 | Peterson | 260/29.6 F |
| 3,544,663 | 12/1970 | Hauptschein et al. | 260/29.6 F |
| 3,836,537 | 9/1974 | Boerwinkle et al. | 260/29.6 HN |
| 3,843,579 | 10/1974 | Eanzel | 260/29.6 RW |

*Primary Examiner*—M. J. Welsh
*Attorney, Agent, or Firm*—Cruzan Alexander; Donald M. Sell; Carolyn A. Bates

[57] ABSTRACT

The invention relates to novel complexes formed by mixing together in an aqueous medium a zwitterionic polymer and a fluorocarbon acid compound. The complex can be formulated with conventional cosmetic extending media to provide solvent-repellent, skin-protective compositions.

16 Claims, No Drawings

SOLVENT REPELLENT COMPLEXES

This invention relates to chemical complexes which are applied to the skin to provide repellent barriers against polar and nonpolar organic solvents. A further aspect of the invention relates to solvent-repellent complexes which contain a fluorocarbon moiety. Also included within the scope of the invention are compositions wherein the fluorocarbon-containing complexes are formulated into cosmetically-acceptable extending media.

Dermal irritation caused by contact with organic solvents presents a significant problem for many people. Workers in a variety of industrial and laboratory occupations are constantly exposed to organic solvents during the course of their normal workday. When the skin of these workers, particularly skin on the hands, is subjected to prolonged exposure to such commonly-used solvents as acetone, gasoline or alcohols, the skin loses some of its natural moisture and fat content and may become chapped and irritated.

Prior to the present invention a number of attempts have been made to provide so-called "dermal protective" compositions which can be applied to the skin to reduce the undesirable effects caused by contact with various irritants. Many of these known compositions contain ingredients intended to form a barrier film on the skin to prevent penetration by irritants. Certain film-forming polymers and copolymers have been used on skin to provide barrier-type protection against various irritants. U.S. Pat. No. 3,749,722 discloses a dermal protective composition based upon an acrylic polymer, and U.S. Pat. No. 3,824,218 discloses a preparation containing a copolymer of a vinyl ester and a monoalkyl ester of maleic anhydride as the active barrier ingredient.

Certain fluorocarbon-containing materials have also been incorporated into skin creams to improve repellency to aqueous and polar organic solvents. U.S. Pat. No. 3,100,180 discloses a dermal-protective composition wherein the active protective ingredient is a fluorine-containing, elastomeric, vinyl-type polymer in which from 10 to 75 percent of the hydrogen atoms directly attached to carbon atoms has been replaced by fluorine. Skin protective agents based on fluorinated silicones are described in U.S. Pat. No. 3,541,205. Skin protective agents prepared by the condensation of aldehydes and fluoroaliphatic phenols are disclosed in U.S. Pat. No. 3,832,230.

While the dermal-protective compositions of the prior art, particularly those containing barrier ingredients, have been somewhat successful in preventing irritation caused by contact with organic solvents and other irritants, they have suffered from a number of disadvantages. Many are not effective against a broad spectrum of solvents, and many do not provide long-lasting protection. Fluorocarbon-containing protective compositions of the prior art, while maintaining their repellent properties somewhat longer, are relatively expensive if they have a high fluorocarbon content, and in some cases are difficult to formulate into cosmetically-acceptable extending media.

The solvent-repellent complexes of the present invention overcome many of the disadvantages associated with dermal-protective agents of the prior art. The complexes of this invention provide repellency to a wide variety of organic solvent materials. They are capable of withstanding repeated exposure to solvents without loosing their repellent properties. They are relatively inexpensive in comparison to the fluorocarbon-containing materials previously known, and, in general, they are easy to formulate into cosmetically-acceptable extending media.

The term "solvent-repellent" as used herein to characterize the complexes of the invention refers to the ability of the complexes, when applied to filter paper, to prevent penetration by fourteen specific organic solvents enumerated hereinbelow.

The solvent-repellent complexes are formed by mixing together in a water medium a fluorocarbon compound having acid functionality or a salt thereof and a water-soluble zwitterionic polymer. The term "complex" simply denotes the reaction product of the fluorocarbon compound and the polymer, the exact chemical nature of which is not known with certainty. In the context of the invention the expressions "zwitterionic polymer" and "zwitterionic monomer" refer to internally neutralized polymers and/or substantially neutralized polymers and monomers containing an acidic carboxylate group and a basic ammonium group. The term "polymer" as used herein refers to the polymerization product of one or more dissimilar monomers, and the term "copolymer" refers to the polymerization product of two or more dissimilar monomers.

The water-soluble zwitterionic polymers which form one component of the complexes of the invention are of two different types. The first type is polymers comprising carboxy betaines having the repeating formula

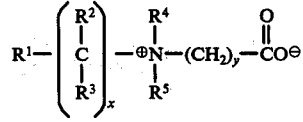

Formula I wherein $R^1$ is acrylate, methacrylate, acrylamide or methacrylamide; $R^2$ and $R^3$ are hydrogen or alkyl having 1 to 3 carbon atoms; $R^4$ and $R^5$ are hydrogen or alkyl having 1 to 6 carbon atoms; x and y are integers from 1 to 3 inclusive. The second type is copolymers comprising monomers (1) and (2) shown below:

1. substituted acidic vinyl monomers of the formula $$CR^7H=CR^8CO_2H \qquad \text{II}$$

wherein $R^7$ is hydrogen or

and $R^8$ is hydrogen, chlorine or $-CH_3$; and 2. substituted basic vinyl monomers having the general formula $$CH_2=CR^6COQ \qquad \text{III}$$

wherein $R^6$ is hydrogen or $-CH_3$ and Q is an organic radical containing a basic nitrogen-containing group. In these copolymers the acidic and basic functionalities are retained in the copolymer structure and the mole ratio of basic monomer to acidic monomer is from 40/60 to 70/30, except where $R^7$ is $$-\overset{O}{\overset{\|}{C}}OH,$$

the mole ratio is 57/43 to 82/18.

The fluorocarbon compounds which form the second component of the complexes are dermally-nonirritating and of two general types. The first type is acid compounds represented by the formula $$(R_f)_d\text{—}(W)_m\text{—}(A)_n \qquad \text{IV}$$

wherein $R_f$ is a monovalent fluorinated saturated non-aromatic aliphatic radical having 5 to 20 carbon atoms in the skeletal chain; W is a polyvalent linking radical free from functional groups which react with water; A is $$-\overset{O}{\overset{\|}{C}}OH,$$

$-SO_3H$, $-OSO_3H$, $$-\overset{}{\underset{\underset{|}{O}}{O}}PO_2H$$

or $-OPO_3H_2$; $d$ is one or two; $m$ is zero or one, $n$ is one or two except when A is $$-\overset{}{\underset{\underset{|}{O}}{O}}P_2H,$$

$m$ may be two, and when $m$ is zero $d$ is one; and salts of said acids. The second type is acid compounds represented by the formula

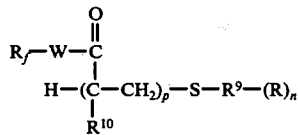

Formula V wherein $R_f$, W, A and $n$ are as defined above, $R^9$ is alkyl having 1 to 4 carbon atoms, $p$ is an integer from 2 to 4 inclusive, designating the same or different $R_f$—W groups; and salts of said acids. Both types of fluorocarbon compounds contain at least 40 percent by weight of fluorine derived from the $R_f$ portion of the molecule. In the complexes the ratio of the amine equivalence of the zwitterionic polymer to the acid equivalence of the fluorocarbon compound is 1/1 to 150/1.

The fluorocarbon-containing complexes can be formulated into a wide variety of cosmetically-acceptable extending media to form dermal-protective compositions.

The general class of water-soluble zwitterionic polymers useful in forming the solvent-repellent complexes and the method of preparing them are known and described in U.S. Pat. No. 3,836,537. This patent discloses these polymers to be useful hair setting agents.

Zwitterionic polymers and copolymers useful in preparing the complexes of the invention are of two general types. The first type is polymers formed from monomers such as beta-methacryloxyethyl beta-dimethyl amino propionate-betaine, wherein ammonium and carboxylate groups are both present in the monomer. These monomers have the general formula

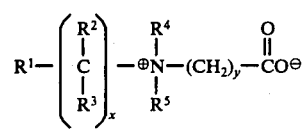

Formula I wherein $R^1$ represents a polymerizable unsaturated group which permits homopolymerization of the monomer or copolymerization with other polymerizable monomers. Such polymerizable unsaturated groups are preferably selected from the group consisting of acrylate, methacrylate, acrylamide and methacrylamide. Subscripts "$x$" and "$y$" each represent an integer from 1 to 3 inclusive to provide methylene, ethylene, or propylene groups in the polymer backbone. Groups larger than 3 carbon atoms will reduce the water solubility of the resultant polymer such that it may not be useful in forming the complexes of the invention. $R^2$ and $R^3$ represent hydrogen, methyl, ethyl or propyl radicals. $R^4$ and $R^5$ represent hydrogen or alkyl groups having 1 to 6 carbon atoms. $R^2$, $R^3$, $R^4$ and $R^5$ necessarily contain lower alkyl groups in order to maintain the requisite water-solubility of the polymer.

Monomers of Formula I may be homopolymerized or copolymerized with other polymerizable monomers to provide zwitterionic polymers which are useful in preparing the solvent-repellent complexes of the invention. When copolymers are used, the zwitterionic moiety of the copolymer should comprise on a molar base about 10%, and preferably 20%, of the copolymer in order to provide sufficient ammonium functionality to complex with the fluorocarbon ingredient of the mixture.

Typical water-soluble, non-zwitterionic monomers suitable for copolymerization with monomers of Formula I are vinyl pyrrolidone, dimethylaminoethyl acrylate, dimethylaminoethyl methacrylate, diethylaminoethyl acrylate and diethylaminoethyl methacrylate.

Other non-zwitterionic monomers which are water-insoluble, such as alkyl acrylates or methacrylates, e.g., methyl acrylate, acrylamides, methacrylamides or vinyl acetate may also be copolymerized with monomers of Formula I to provide copolymers useful in forming the solvent-repellent complexes of the invention. However, substantially less water-insoluble nonzwitterionic monomer is utilized so as to retain the requisite water solubility of the copolymer.

The second type of zwitterionic copolymers useful in preparing the solvent-repellent complexes of the invention are formed from the copolymerization of (1) monomers having amine functionality and (2) monomers having acid carboxylate functionality.

The acidic monomers are preferably substituted vinyl compounds of the general formula $$CR^7H\!=\!CR^8CO_2H \qquad \text{II}$$

wherein $R^7$ is hydrogen or $-CO_2H$, and $R^8$ is hydrogen, chlorine or methyl. Exemplary compounds of this type include acrylic acid, methacrylic acid, maleic acid and α-chloroacrylic acid. The basic monomers are preferably substituted vinyl compounds of the formula $$CH_2\!=\!CR^6COQ \qquad \text{III}$$

wherein $R^6$ is hydrogen or methyl, and Q is an organic radical containing a basic nitrogen-containing group. Examples of these monomers include dialkyl aminoalkyl methacrylates such as dimethylaminoethyl methacrylate, and dialkyl aminoalkyl acrylates.

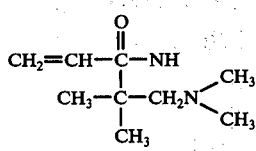

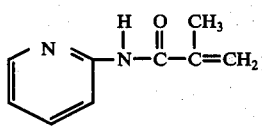

Preferably the Q-portion of the compounds of Formula III is either —O—CH$_2$CH$_2$—NR$^{11}$ or $$-\overset{H}{N}-CH_2CH_2-NR^{11}$$

wherein $R^{11}$ is methyl, ethyl or propyl. The preferred zwitterionic copolymers of this second type are formed from monomers of acrylic acid or methacrylic acid polymerized with monomers of dimethylaminoethyl methacrylate or diethylaminoethyl acrylate.

Generally the mole ratio of basic monomer (Formula III) to acidic monomer (Formula II) in the aforementioned zwitterionic copolymers ranges from 70/30 to 40/60, and preferably 50/50. In the case of difunctional acidic monomers having two carboxylate groups, the mole ratio of basic monomer to acidic monomer will range from 57/43 to 82/18. The resultant copolymer is preferably completely neutralized, although partially neutralized copolymers are also useful.

Zwitterionic copolymers of this type, may also include monomers which do not contain acidic or basic groups and which may be added to reduce cost. Such monomers typically include lower alkyl acrylates or methacrylates, e.g., methyl acrylate, and acrylamides or methacrylamides. The neutral monomers, which can be water-soluble or water-insoluble, will be contained in the copolymer in proportions which do not adversely affect the water-solubility of the resultant copolymer.

As indicated above the zwitterionic polymer or copolymer provides one major component of the solvent-repellent complexes of the invention. The second major component of the complex is a fluorocarbon compound containing one or two acidic functional groups or salts thereof. These compounds are commercially available or readily prepared from commercial materials by conventional chemical reactions.

The first type of fluorocarbon compound is represented by the formula

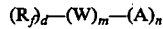    IV wherein $d$ is one or two and $R_f$ is a monovalent fluorinated saturated non-aromatic aliphatic radical having 5 to 20 carbon atoms in the skeletal chain. This chain may be straight, branched or cyclic, and may be interrupted by divalent oxygen atoms or trivalent nitrogen atoms bonded to carbon atoms. Preferably, the chain does not contain more than one nitrogen atom or one oxygen atom for every two carbon atoms in the skeletal chain.

A perfluoroalkyl radical is preferred, but an occasional hydrogen or chlorine atom may be present in the fluoroaliphatic radical provided that not more than one such non-fluorine substituent is present in such radical for every two carbon atoms, and that such radical contains a terminal perfluoroalkyl group. "Terminal" in this connection refers to the position in the skeletal chain of the radical which is furthest removed from the W-substituent. Preferably, such radical contains not more than 20 carbon atoms since such a large radical reduces the dispersability of the compound in water and also results in inefficient use of the fluorine content.

The W-substituent of Formula IV is a polyvalent linking radical, and $m$ is zero or one. This linking group has no recognizable effect on the repellent properties of the complex, and in fact, the W-substituent may be entirely omitted as in the case where $m$ is zero.

When present, the W-substituent may have almost infinitely varied structures and it will be either di- or tri-valent depending on the number of A-substituents present. The size of W-substituent is necessarily limited, however, due to the fact the overall molecule should comprise at least 40 percent by weight of fluorine derived from the $R_f$ portion. Thus, a large W-substituent may require an impractically large $R_f$ group to satisfy this limitation. Additionally, the W-substituent must be water-stable, i.e., it must not contain functional groups which react with water.

The polyvalent linking radicals constituting the presently preferred W-substituents are

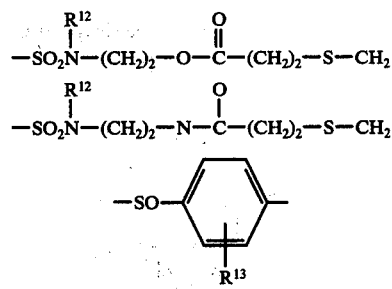

wherein $R^{12}$ is hydrogen or alkyl having 1 to 4 carbon atoms and $R^{13}$ is hydrogen, $R^{12}$, —OH or —OR$^{12}$. Also preferred are compounds of formula IV wherein $m$ is zero and W is not present.

The A-substituent of Formula IV represents the acidic portion of the molecule and may be

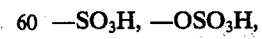

or —OPO$_3$H$_2$, and $n$ is one or two. In the compounds of formula IV wherein A is $-OP_2H$,

$m$ may be two. Additionally, in those compounds wherein $m$ is zero, $d$ is one. Also included within this class of fluorocarbon compounds are salts formed by the reaction of the acid group or groups of these compounds with an organic or inorganic base.

Typical examples of fluorocarbon compounds of Formula IV useful in preparing the complexes of the invention are shown in the following Table I.

TABLE I

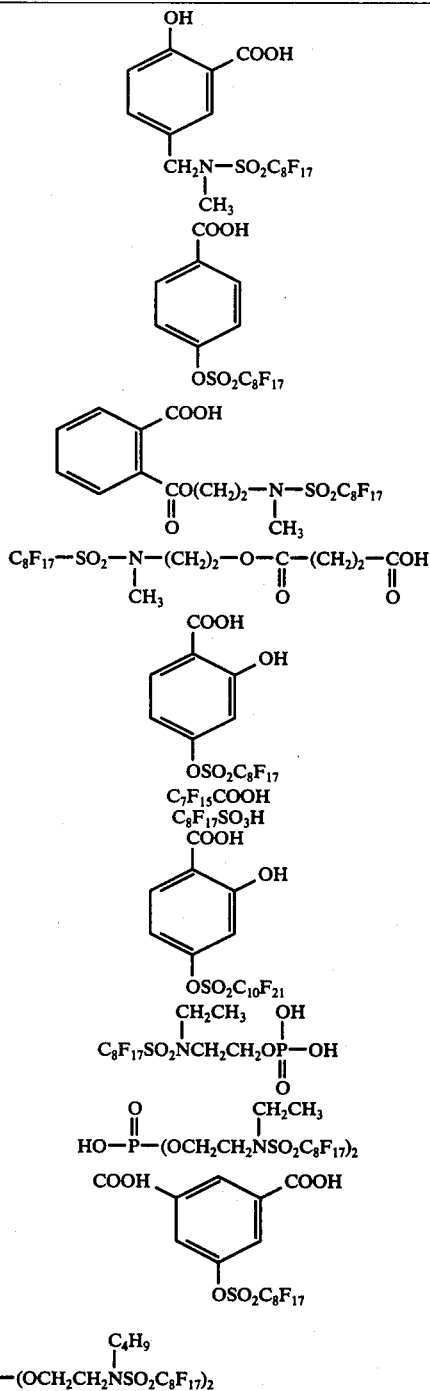

TABLE I-continued $$HO-\overset{O}{\underset{\|}{P}}-(OCH_2(CH_2)_{10}\overset{C_2H_5}{\underset{|}{N}}SO_2C_{18}F_{37})_2$$

$$C_8F_{17}SO_2\overset{C_2H_5}{\underset{|}{N}}CH_2CH_2O-\overset{O}{\underset{\|}{P}}-OCH_2CH_2\overset{O}{\underset{\|}{C}}C_8F_{17}$$
$$\underset{OH}{|}$$

$$HO-\overset{O}{\underset{\|}{P}}-[OCH_2(CH_2)_{10}\overset{O}{\underset{\|}{C}}C_{18}F_{37}]_2$$

$$HO-\overset{O}{\underset{\|}{P}}-[O(CH_2CH_2CH_2CH_2-O)_2-CH_2C_{18}F_{37}]_2$$

$HOOC-(CH_2)_8-\overset{C_2H_5}{\underset{|}{N}}SO_2C_8F_{17}$ $HOOC-(CH_2)_{11}-\overset{C_4H_9}{\underset{|}{N}}SO_2C_{18}F_{37}$ $HOOC-(CH_2)_{10}-\overset{C_2H_5}{\underset{|}{N}}SO_2C_{12}F_{25}$ $HOOC-(CH_2)_3\overset{O}{\underset{H\|}{N}}CC_8F_{17}$ $HOOC-(CH_2)_3\overset{O}{\underset{H\|}{N}}CC_8F_{37}$ $HOOC-CH_2C_8F_{17}$ $HOOC-CH_2-CH_2-S-CH_2CH_2-\overset{CH_3}{\underset{|}{N}}SO_2C_8F_{17}$ $HOOC-\overset{C_2H_5}{\underset{|}{CH}}-CH_2-S-CH_2(CH_2)_7-\overset{}{N}SO_2C_{12}F_{25}$
$\underset{CH_3}{|}$ $HOOC-CH_2-CH_2-S-CH_2(CH_2)_{10}-\overset{C_4H_9}{\underset{|}{N}}SO_2C_{18}F_{37}$ $HOOC-\underset{CH_3}{\overset{H}{\underset{|}{CH}}}-CH_2-S-CH_2(CH_2)_7-\overset{}{N}-\overset{O}{\underset{\|}{C}}C_{18}F_{37}$ $HOOC-CH_2-CH_2-S-CH_2(CF_2)_2CH_2OC_8F_{17}$
$HOOC-CH_2-CH_2-S-CH_2(CF_2)_2CH_2OC_{12}F_{25}$
$HOOC-\overset{}{\underset{CH_3}{\overset{|}{CH}}}-CH_2-S-(CH_2)_8CHClCH_2C_{18}F_{37}$ $HOOC-CH_2-CH_2-S-$ 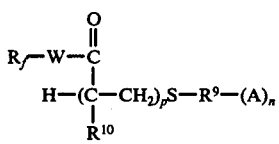

The second type of fluorocarbon compound useful in forming the complexes of the invention are acidic oligomeric materials represented by the formula Formula V $$R_f-W-\overset{O}{\underset{\|}{C}}$$
$$H-(\overset{}{\underset{R^{10}}{\overset{|}{C}}}-CH_2)_pS-R^9-(A)_n$$

wherein $R_f$, W, A and $n$ are as defined in Formula IV above; $R^9$ is alkyl having one to six carbon atoms; $R^{10}$ is $CH_3$ or H; and $p$ is an integer from two to four, inclusive, designating the same or different $R_f$—W groups. Also included in this type of fluorocarbon compound are salts of the acids.

Oligomers of Formula V are prepared by free radical polymerization of monomers of the type

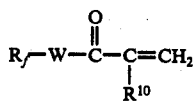

in the presence of a thiol acid of the type HS—$R^9$—A. The oligomers may be formed from the same or dissimilar monomers. The average degree of polymerization (p) is determined by the ratio of monomer to thiol acid charged. Examples of fluorochemical monomers which can be polymerized with thio acids to form oligomers of Formula V are shown in the following Table II.

TABLE II $$CH_2=C(R^{10})-C(=O)-O-CH_2CH_2-N(CH_3)SO_2C_8F_{17}$$

$$CH_2=C(R^{10})-C(=O)-O-CH_2(CH_2)_{10}-N(C_2H_5)SO_2C_8F_{17}$$

$$CH_2=C(R^{10})-C(=O)-O-CH_2(CH_2)_7-N(C_4H_9)SO_2C_{18}F_{37}$$

$$CH_2=C(R^{10})-C(=O)-O-CH_2CH_2-C(=O)C_8F_{17}$$

$$CH_2=C(R^{10})-C(=O)-O-CH_2(CH_2)_{10}-C(=O)C_8F_{17}$$

$$CH_2=C(R^{10})-C(=O)-O-CH_2(CH_2)_7-C(=O)C_{16}F_{33}$$

$$CH_2=C(R^{10})-C(=O)-O-(CH_2CH_2O)_2-CH_2-C_8F_{17}$$

$$CH_2=C(R^{10})-C(=O)-O-(CH_2)_6-C_8F_{17}$$

$$CH_2=C(R^{10})-C(=O)-O-CH_2CH_2-N(C_2H_5)C(=O)C_8F_{17}$$

$$CH_2=C(R^{10})-C(=O)-O-(CH_2CH_2CH_2CH_2O)_2-CH_2-C_{18}F_{37}$$

$$CH_2=C(R^{10})-C(=O)-O-\text{C}_6H_4-OSO_2C_8F_{17}$$

$$CH_2=C(R^{10})-C(=O)-N(H)-CH_2CH_2-N(CH_3)SO_2C_8F_{17}$$

TABLE II-continued $$CH_2=C(R^{10})-C(=O)-N(H)-CH_2(CH_2)_{10}-N(C_4H_9)SO_2C_{18}F_{37}$$

$$CH_2=C(R^{10})-C(=O)-N(H)-CH_2CH_2-N(C_2H_5)-C(=O)C_8F_{17}$$

$$CH_2=C(R^{10})-C(=O)-N(H)-CH_2(CH_2)_7-N(C_2H_5)-C(=O)C_{18}F_{17}$$

$$CH_2=C(R^{10})-C(=O)-N(H)-CH_2CH_2-C(=O)-C_8F_{17}$$

$$CH_2=C(R^{10})-C(=O)-N(H)-CH_2(CH)_{10}-C(=O)C_{18}F_{37}$$

$$CH_2=C(R^{10})-C(=O)-N(H)-(CH_2CH_2-O)_2CH_2CH_2N(C_4H_9)SO_2C_8F_{17}$$

$$CH_2=C(R^{10})-C(=O)-N(H)-(CH_2CH_2CH_2CH_2-O)_2CH_2C_8F_{17}$$

$$CH_2=C(R^{10})-C(=O)-N(H)-CH_2CH_2(CF_2)_2CH_2C_8F_{17}$$

$$CH_2=C(R^{10})-C(=O)-N(H)-\text{C}_6H_4-OSO_2C_8F_{17}$$

It is well known in the art that salts of organic acids can be readily prepared by reacting the acid with an organic or inorganic base. In the context of the present invention salts of the fluorocarbon acids of formulas IV and V may be complexed with zwitterionic polymers to prepare solvent-repellent products. Since the complexes are designed for use on the skin and must be dermally-nonirritating. Only those salts are contemplated which are nontoxic or nonirritating to normal skin. The preferred salts are amine salts such as those formed with aminomethylpropanone diol, and alkaline earth salts such as those formed with Na+, K+, etc. In general the salts of the free acids are less preferred than the acids as the latter provide complexes exhibiting greater protection against solvent penetration.

Complexes of the invention are formed by adding the fluorocarbon compound to an aqueous solution containing the water soluble zwitterionic polymer. The mixture is heated under steam to a temperature of 60° to 90° C and rapidly agitated for 1 to 2 hours.

The fluorocarbon compound complexes with the zwitterionic polymer. The exact nature of chemical interaction between these two ingredients is not known. As the complex forms, the fluorocarbon compound is drawn into the aqueous solution by the polymer and a homogeneous mixture develops which exhibits properties different from either of the precursor ingredients. This mixture contains 75 to 99 percent water, is stable and can be further diluted.

The ratio of polymer to fluorocarbon compound in the mixture can be varied greatly depending upon the particular starting materials used. Generally, the ratio of the amine equivalence of the polymer to the acid equivalence of the fluorocarbon will be about 1/1 to 150/1 respectively, and preferably 3/1 to 20/1.

The viscosity of the various mixtures formed by the interaction of the fluorocarbon compound and polymer precursors will vary over a wide range depending upon the starting materials and the ratio of the components of the complex. Mixtures having viscosities of 100 cps to several thousand cps will generally be produced.

Complexes of the invention are readily incorporated into conventional cosmetic extending media to form solvent-repellent compositions suitable for application to the skin. These cosmetic formulation are normally of the oil in water emulsion type, and the complexes are added to the water phase of the emulsion system. It is well known in the art that a variety of ingredients such as emulsifying agents (e.g., triethanolamine and glyceral monostearate); moisturizing and thickening agents such as glycerol, sorbitol, manitol, mineral oil, petrolatum, bees wax etc., can be included in cosmetic formulations to enhance their appeal to the user. Other cosmetically acceptable ingredients such as buffering agents, opacifying agents, fragrances and preservatives may also be included.

It is also contemplated that ingredients such as ultraviolet-light screening compounds, e.g., glyceryl p-aminobenzoate, methyl salicylate or butyl p-hydroxycinnamate; and therapeutic agents such as antibacterial and antifungal agent may be incorporated into the solvent-repellent compositions.

The solvent-repellent complexes of the invention may be incorporated singly or in combination into cosmetically acceptable extending media. Since these complexes are believed to manifest their protective properties by providing a physical barrier to penetration by solvents, it is not necessary that the agents be used in pure form. The solvent-repellent complex is normally present in the composition in an amount ranging from 1 to 20% by weight of the composition, and preferably between 2 and 10% by weight of the composition.

The solvent-repellent properties of the complexes of the invention and formulations thereof were ascertained by two basic tests. These tests provide a measure of the barrier properties of the complexes. The first test method involves coating a standard amount of the test material onto the surface of #5 Whatman filter paper. The treated filter paper is then dried in an oven. Drops of 14 different solvents are placed on the treated filter paper. The drops are observed for a maximum of 5 minutes, and the time of penetration by each drop is recorded. Penetration is noted when a drop wets the paper, i.e. the paper beneath the drop becomes darkened. A maximum score of five for any one solvent indicates no penetration during the period of the test. A test material having a perfect score of 70 indicates no penetration by any of the fourteen different solvents. A score is assigned each test material expressed as "percent penetration", which is calculated according to the formula $100[(1-(\Sigma Pn/70)]$ wherein $\Sigma Pn$ is the sum of the individual penetration times for each solvent.

The term "solvent-repellent" as used to describe the complexes of the invention implies complexes which exhibit less than 40% penetration when subjected to the filter paper test. (This test is described in greater detail in the examples below.)

The second method used to determine the solvent-repellent properties of the complexes of the invention involves measuring contact angles formed by various solvents when placed on the surface of pigskin treated with the test material. All of the complexes of the invention are successful in causing the formation of high contact angles between the solvent droplets and the pigskin surface. This indicates the ability of the complexes to repel organic solvents. (This test is also discussed in detail in the examples below.)

The solvent-repellent complexes of the invention and cosmetic formulations thereof are illustrated by the following non-limiting examples:

EXAMPLE 1

To a solution of 4.08 g of dimethylaminoethyl methacrylate/acrylic acid copolymer (DMAEMA/AA in a 51/49 ratio) in 93 g of water were added 3 g of the p-perfluorosulfonate ester of salicyclic acid having the formula

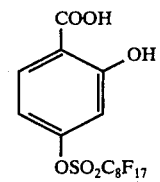

The mixture was heated at 80° C in a steam jacketed resin flask for two hours with rapid agitation. The mixture was cooled with continued agitation until it reached room temperature. A gel developed which had a pH of 4.6 and a viscosity of 15,708 cps.

Large pieces of raw pigskin were washed lightly with soap and water (to remove excess surface fats,) rinsed, lightly patted with a tissue, and air dried approximately 20 minutes. The complex prepared above was then applied to the pigskin with a cotton swab to lightly coat the surface. The treated pigskin was allowed to dry until it felt dry to the touch, or about 20 minutes. One drop each of fourteen different solvents were applied to the treated pigskin. Approximately 60 seconds layer, the contact angles formed between each solvent drop and the surface of the pigskin were measured visually. Scores were assigned to each drop according to a rating scale of 0 to 6 depending upon the size of the contact angle, with higher ratings indicating greater repellency. The approximate size of the contact angles and their assigned ratings were as follows:

| Contact Angle | Rating |
|---|---|
| 100–120° | 6 |
| 90–100° | 5 |
| 60–90° | 4 |
| 40–60° | 3 |
| 20–40° | 2 |
| 1–20° | 1 |
| Spreading | 0 |

Results of this test are shown in the table below.
Also shown in the table are results of the filter paper penetration test performed with the above complex using the same set of fourteen solvents. According to the test procedure 0.75 g of the complex was applied to 61.35 cm² of a piece of #5 Whatman filter paper. The treated filter paper was placed in an oven at 78° C for 15 minutes and the resultant dry coating weight was 0.0532g/61.35 cm². Drops of each solvent were then applied to the treated filter paper and observed for a period of five minutes. The penetration time for each solvent was recorded. Penetration was noted when the drop of solvent wetted the paper, i.e. when the paper beneath the solvent showed any sign of darkening. If no penetration occurred with a given solvent during the five-minute period, a maximum score of 5 was assigned for that solvent. A perfect score against all fourteen solvents would be 70. An average score was calculated for the test material and expressed as "percent penetration." Percent penetration is calculated according to the formula $100[(1-(\Sigma Pn/70)]$ wherein $\Sigma Pn$ is the sum of the individual penetration times for the fourteen solvents. Results are shown in the following table.

TABLE III

| Solvent | Penetration Time (min) | Contact Angle Rating |
|---|---|---|
| Isopropyl alcohol | 5 | 2+ |
| Mineral Spirits | 5 | 3 |
| Trichloromethane | 5 | 3− |
| Xylene | 4.5 | 3+ |
| Gasoline | 5 | 3− |
| Tetrachloroethane | 5 | 3+ |
| Turpentine | 5 | 5+ |
| Methanol | 4.75 | 3 |
| Nujol | 5 | 4 |
| Ethyl Acetate | 5 | 2 |
| Triethyline tetraamine | 2.5 | 4 |
| Benzyl alcohol | 4.5 | 3 |
| Acetone | 5 | 2 |
| *Detergent | 4.5 | 5 |
| % penetration = 6.6 | | $\bar{m}$ = 3.1 |

*0.5% aqueous solution of sodium lauryl sulfate

EXAMPLE 2

A three neck round bottom flask equipped with a mechanical stirrer was charged with 23.80g (0.039 moles) of

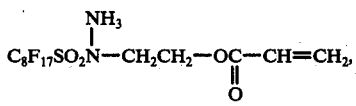

1.20 g thioglycolic acid, and 75.0 ml of acetone. A vacuum was applied to the flask until the contents boiled. The vacuum was broken with nitrogen after five minutes and the contents were heated to reflux under nitrogen. The flask was then opened under positive N₂ pressure and 0.1875g azobisisobutyronitrile (VAZO 64) was added. The flask was closed and reflux was continued for 16 hours. The reaction mixture was then poured into 600 ml of cold distilled water and the product

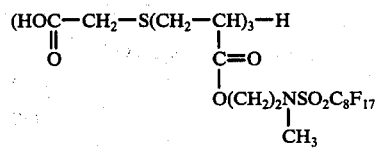

precipitated. The product was washed with water until the odor of TGA was removed and dried under vacuum and slight heating for 24 hours. Two grams of the product were added to 12g of dimethylaminoethyl methacrylate/acrylic acid copolymer (DMAEMA/AA 51/49) which had been diluted in 86 g of H₂O to form a 24% solution. The mixture was agitated and heated with steam for 2 hours with a pot temperature of 75°–80° C. Agitation was continued while the system was allowed to cool to room temperature.

The product was tested according to the methods described in example 1. It was found to have an average contact angle rating of 3.14, and its percent penetration score when applied to filter paper (0.0445 g/61.35 cm² dry coating weight) was 2.9.

EXAMPLE 3

Two grams of the oligomeric fluorochemical acid

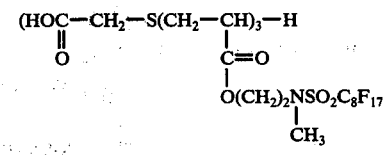

prepared as described in Example 2, was added 47.92 g of water and 0.08 g of NaOH producing a mixture having a mole equivalent ratio of acid to base of 1:1. The mixture was heated for 30 minutes at 60° C with rapid agitation until a clear solution developed. The solution was cooled to room temperature, and 12 g of dimethylaminoethyl methacrylate/acrylic acid copolymer (51/49) in 38 g of water was added to the solution. The mixture was agitated and stirred until a homogeneous mixture developed. The acid/amine equivalent ratio of the product was 1/12. The product was tested according to the filter paper penetration test described in Example 1 and was found to to have a percent penetration of 37.2 (0.04149 g/61.35 cm² dry coating weight.

EXAMPLES 4–21

Using the methods of preparation of Examples 1 and 2 the following complexes of the invention were prepared.

TABLE IV

| Example No. | Polymer Composition Monomer | Mole Ratio | Fluorochemical | Weight Ratio FC/Polymer[1] (grams) | Equivalent Ratio FC/Polymer | pH |
|---|---|---|---|---|---|---|
| 4. | DMAEMA/AA[2] | 51/49 | C₈F₁₇SO₃H | 2.0/4.32 | 1/4.72 | 4.1 |
| 5. | DMAEMA/AA | 51/49 | C₇F₁₅CO₂H | 1/4 | 1/7.23 | 4.4 |
| 6. | DMAEMA/AA | 51/49 | 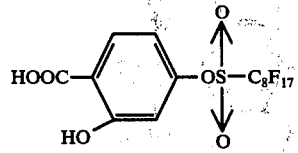 | 3/4.08 | 1/3.78 | 4.6 |

TABLE IV-continued

| Example No. | Polymer Composition Monomer | Mole Ratio | Fluorochemical | Weight Ratio FC/Polymer[1] (grams) | Equivalent Ratio FC/Polymer | pH |
|---|---|---|---|---|---|---|
| 7. | DMAEMA/AA | 51/49 | 4-HOOC-3-HO-C$_6$H$_3$-O-SO$_2$-C$_6$F$_{17}$ | 2/4.08 | 1/4.8 | 4.6 |
| 8. | DMAEMA/AA | 51/49 | 3,5-(HOOC)$_2$-C$_6$H$_3$-O-SO$_2$-C$_8$F$_{17}$ | 1.5/4.1 | 1/8 | 4.6 |
| 9. | DMAEMA/AA | 51/49 | C$_8$F$_{17}$SO$_2$N(CH$_3$)—(CH$_2$)$_2$—O—(CH$_2$)$_2$—S—CH$_2$COOH | 0.5/23.9 | 1/142 | 5.5 |
| 10. | DMAEMA/AA | 51/49 | 4-HOOC-3-HO-C$_6$H$_3$-O-SO$_2$-C$_8$F$_{17}$ | 0.5/23.9 | 1/133 | 5.3 |
| 11. | DMAEMA/AA | 51/49 | C$_8$F$_{17}$SO$_3$H | 0.5/24 | 1/104 | 5.7 |
| 12. | DMAEMA/AA | 51/49 | N-MethylFOSEA/TGA 75/25 | 0.5/4.2 | 1/71.5 | 5.4 |
| 13. | DMAEMA/AA | 51/49 | N-MethylFOSEA/TGA 75/25 | 2/1.92 | 1/2.67 | 5.1 |
| 14. | DMAEMA/AA | 51/49 | N-EthylFOSE—O—P(=O)(OH)$_2$ [3] | 3/4.2 | 1/4 | 5.5 |
| 15. | DMAEMA/AA | 51/49 | N-EthylFOSE—O—P(=O)(OH)—O—NEthylFOSE [4] | 3/2.3 | 1/4 | 7.1 |
| 16. | DMAEMA/MA[5] | 51/49 | 4-HOOC-3-HO-C$_6$H$_3$-O-SO$_2$-C$_8$F$_{17}$ | 3.5/4.75 | 1/3.54 | 4.6 |
| 17. | DEAEA/MA[6] | 51/49 | 4-HOOC-3-HO-C$_6$H$_3$-O-SO$_2$-C$_8$F$_{17}$ | 3.5/4.75 | 1/3.4 | 5.3 |
| 18. | Betaine[7] | (homopolymer) | 4-HOOC-3-HO-C$_6$H$_3$-O-SO$_2$-C$_8$F$_{17}$ | 3/4.22 | 1/3.9 | 4.2 |
| 19. | DMAEMA/AA | 51/49 | 4-HOOC-3-HO-C$_6$H$_3$-O-SO$_2$-C$_{10}$F$_{21}$ | 1/4.2 | 1/13.6 | 5.9 |
| 20. | DMAEMA/AA | 70/30 | 4-HOOC-3-HO-C$_6$H$_3$-O-SO$_2$-C$_8$F$_{17}$ | 3/4.72 | 1/4.77 | 3.5 |
| 21. | DMAEMA/AA | 60/40 | 4-HOOC-3-HO-C$_6$H$_3$-O-SO$_2$-C$_8$F$_{17}$ | 3/4.22 | 1/4.34 | 4.1 |

TABLE IV-continued

| Example No. | Polymer Composition Monomer | Mole Ratio | Fluorochemical | Weight Ratio FC/Polymer[1] (grams) | Equivalent Ratio FC/Polymer | pH |
|---|---|---|---|---|---|---|
| 22. | DMAEMA/AA | 40/60 | 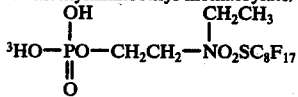 | 2/4.22 | 1/5.06 | 4.4 |
| 23. | DMAEMA/AA | 51/49 | 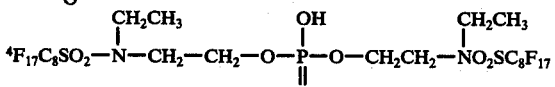 | 1.13/15.0 | 1/10.42 | 6.8 |
| 24. | DMAEMA/AA | 51/49 | 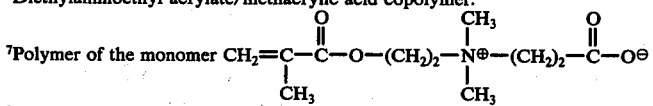 | 4.8/24.7 | 1/3.54 | 6.5 |

[1] Water is added to make a total of 100 g of mixture.
[2] Dimethylaminoethyl methacrylate/acrylic acid copolymer.
[3] $\overset{OH}{HO-\underset{\underset{O}{\|}}{P}-O}-CH_2CH_2-\overset{CH_2CH_3}{N}O_2SC_8F_{17}$
[4] $F_{17}C_8SO_2-\overset{CH_2CH_3}{N}-CH_2-CH_2-O-\overset{OH}{\underset{\underset{O}{\|}}{P}}-O-CH_2CH_2-\overset{CH_2CH_3}{N}O_2SC_8F_{17}$
[5] Dimethylaminoethyl methacrylate/methacrylic acid copolymer.
[6] Diethylaminoethyl acrylate/methacrylic acid copolymer.
[7] Polymer of the monomer $CH_2=\overset{CH_3}{\underset{CH_3}{C}}-\overset{O}{\overset{\|}{C}}-O-(CH_2)_2-\overset{CH_3}{\underset{CH_3}{N^\oplus}}-(CH_2)_2-\overset{O}{\overset{\|}{C}}-O^\ominus$
[8] Salt formed by reacting 1 mole equivalent of the acid with 1 mole equivalent of 2-amino-2-methyl propanol.

The above complexes were each tested for solvent repellency according to the methods described in Example 1. Additionally, the preferred zwitterionic polymer and fluorocarbon compound were each tested along to show that the repellency obtained with the complex is significantly better than that obtained with each component alone. The results are shown in the following Table V.

TABLE V

| Complex (Example No) | Dry Coating Weight On Filter Paper (g/61.35 cm²) | % Penetration | Average Contact Angle Rating |
|---|---|---|---|
| 4 | .0482 | 11.6 | 2.75 |
| 5 | .0482 | 6.8 | 2.60 |
| 6 | .0532 | 6.6 | 3.14 |
| 7 | .0721 | 28.0 | 3.21 |
| 8 | .0425 | 30.0 | 2.85 |
| 9 | .1322 | 7.2 | 3.28 |
| 10 | .0860 | 34.4 | 2.85 |
| 11 | .1200 | 3.0 | 2.82 |
| 12 | .0515 | 22.2 | 2.68 |
| 13 | .0200 | 1.4 | 3.11 |
| 14 | .0497 | 3.0 | 4.14 |
| 15 | .0524 | 6.0 | 4.17 |
| 16 | .0548 | 5.4 | 2.90 |
| 17 | .0691 | 5.4 | 3.00 |
| 18 | .0664 | 4.3 | 3.57 |
| 19 | .0460 | 31.3 | 3.44 |
| 20 | .0400 | 21.5 | 3.57 |
| 21 | .0858 | 1.0 | 3.68 |
| 22 | .0324 | 5.0 | 3.75 |
| DMAEMA/AA (51/49) | .0400 | 99.9 | 1.14 |
| 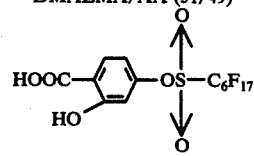 | .0220 | 82.4 | 2.1 |
| 23 | .0512 | 28.7 | — |
| 24 | .0496 | 39.1 | — |

The following examples illustrate the formulation of complexes of the invention with cosmetically-acceptable extending media to prepare compositions suitable for application to the skin.

EXAMPLE 25

A composition containing the following ingredients was prepared:

| A. Water Phase | Weight (grams) |
|---|---|
| 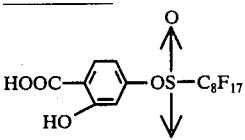 | 3.21 |
| DMAEMA/AA (51/49) | 4.22 |
| Deionized Water | 78.23 |
| B. Oil phase | |
| Mineral Oil | 4.31 |
| Glycerol monostearate | 3.22 |
| Petrolatum | 3.22 |
| Magnesium stearate | 3.22 |
| *Dowicil® 200 (preservative) | .34 |
| **Fragrance | .03 |

*Cis isomer of 1-(3-chloroallyl)-3,5,7-triazo-1-azoniaadamontane chloride from Dow Chemical Co., Midland, Michigan.
**PA-41952 Perfume Oil from Givandan Corporation.

The fluorocarbon compound, polymer and water were mixed together in a steam jacketed flask and heated at 80° C with rapid agitation for approximately two hours, and a homogeneous mixture developed.

Glycerol monostearate, petrolatum, magnesium stearate and mineral oil were mixed together and heated to 100° C until an oil phase developed. The oil phase was added slowly to the water phase with rapid agitation. The mixture was kept at 80° C and stirred for one hour. Stirring was continued and the temperature was allowed to drop to room temperature. Dowicil®, dissolved in a small quantity of water, was added at 35° C, and the fragrance was added at 30° C. The resulting composition was cosmetically appealing and pleasant to apply to the skin.

The composition was tested according to the filter paper penetration and contact angle tests described in example 1. The composition had a contact angle rating of 3.35 and the precent penetration when applied to filter paper (0.1 59g/61.35 cm²) was 7.6.

EXAMPLE 26

Following the method of example 23 the following formulation was prepared.

| Ingredients | Weight (grams) |
|---|---|
| A. Water phase | |
| DMAEMA/AA (51/49) | 4.1 |
| 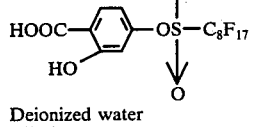 | 3.0 |
| Deionized water | 78.03 |
| B. Oil phase | |
| Petrolatum | 4.75 |
| Mineral Oil | 5.5 |
| Stearic Acid | 3.5 |
| Triethanolamine | 1.125 |

The composition was cosmetically appealing and pleasant to apply to the skin. When tested according to the filter paper test described in example 1 (0.190g/61.35 cm²) the composition had a percent penetration of 31.6.

What is claimed is:

1. Complex formed by mixing together in an aqueous medium a water-soluble zwitterionic polymer selected from the group consisting of
   a. polymers comprising carboxy betaines having the repeating formula

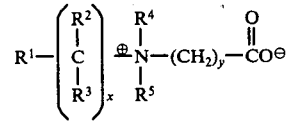

wherein $R^1$ is acrylate, methacrylate, acrylamide or methacrylamide; $R^2$ and $R^3$ are hydrogen or alkyl having 1 to 3 carbon atoms; $R^4$ and $R^5$ are hydrogen or alkyl having 1 to 6 carbon atoms; $x$ and $y$ are integers from 1 to 3 inclusive;

b. copolymers comprising monomers (1) and (2) shown below:
   1. substituted acidic vinyl monomers of the formula $CR^7H = CR^8CO_2H$ wherein $R^7$ is hydrogen or

and $R^8$ is hydrogen, chlorine or $-CH_3$; and
   2. substituted basic vinyl monomers having the general formula $CH_2 = CR^6COQ$ wherein $R^6$ is hydrogen or $-CH_3$, and Q is an organic radical containing a basic nitrogen-containing group, wherein said acidic and basic functionalities are retained in the copolymer structure and wherein the mole ratio of basic monomer to acidic monomer in said copolymer is from 40/60 to 70/30, except where $R^7$ is

the mole ratio is 57/43 to 82/18, with a fluorocarbon compound selected from the group consisting of
   a. $(R_f)_d-(W)_m-(A)_n$ wherein $R_f$ is a monovalent fluorinated saturated non-aromatic aliphatic radical having 5 to 20 carbon atoms in the skeletal chain; W is a polyvalent linking radical free from functional groups which react with water; A is

$-SO_3H, -OSO_3H,$

or —OPO$_3$H$_2$; $d$ is one or two; $m$ is zero or one, $n$ is one or two, except when A is $$-\text{OP}_2\text{H},\overset{\text{O}}{\underset{|}{}}$$

$m$ may be two, and when $m$ is zero $d$ is one, and salts thereof, said compound containing at least 40 percent by weight of fluorine derived by the R$_f$ portion; and (b) 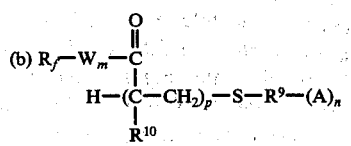

wherein R$_f$, W, A and $n$ are as defined above, R$^9$ is alkyl having 1 to 4 carbon atoms R$^{10}$ is hydrogen or methyl, $p$ is an integer from 2 to 4, inclusive, designating the same or different R$_f$-W groups; and salts thereof said compound containing at least 40 percent by weight of fluorine derived from the R$_f$ portion;
wherein the ratio of the amine equivalence of said zwitterionic polymer to the acid equivalence of said fluorocarbon is 1/1 to 150/1.

2. Dermally non-irritating solvent-repellent complex formed by mixing together in an aqueous medium a water-solublle zwitterionic polymer selected from the group consisting of
  a. polymers comprising carboxy betaines having the repeating formula

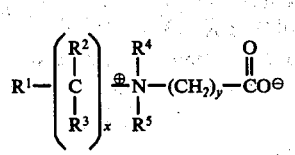

wherein R$^1$ is acrylate, methacrylate, acrylamide or methacrylamide; R$^2$ and R$^3$ are hydrogen or alkyl having 1 to 3 carbon atoms; R$^4$ and R$^5$ are hydrogen or alkyl having 1 to 6 carbon atoms; $x$ and $y$ are integers from 1 to 3 inclusive;
  b. copolymers comprising monomers (1) and (2) shown below:
    1. substituted acidic vinyl monomers of the formula

CR$^7$H=CR$^8$CO$_2$H wherein R$^7$ is hydrogen or $$-\overset{\text{O}}{\overset{\|}{\text{C}}}\text{OH},$$

and R$^8$ is hydrogen, chlorine or —CH$_3$; and
    2. substituted basic vinyl monomers having the general formula

CH$_2$=CR$^6$COQ wherein R$^6$ is hydrogen or —CH$_3$, and Q is an organic radical containing a basic nitrogen-containing group, wherein said acidic and basic functionalities are retained in the copolymer structure and wherein the mole ratio of basic monomer to acidic monomer in said copolymer is from 40/60 to 70/30, except where R$^7$ is $$-\overset{\text{O}}{\overset{\|}{\text{C}}}\text{OH},$$

the mole ratio is 57/43 to 82/18 with a fluorocarbon compound selected from the group consisting of
  a. (R$_f$)$_d$—(W)$_m$—(A)$_n$ wherein R$_f$ is a monovalent fluorinated saturated non-aromatic aliphatic radical having 5 to 20 carbon atoms in the skeletal chain; W is a polyvalent linking radical free from functional groups which react with water; A is $$-\overset{\text{O}}{\overset{\|}{\text{C}}}\text{OH},$$

—SO$_3$H, —OSO$_3$H, $$-\text{OPO}_2\text{H}\overset{\text{O}}{\underset{|}{}}$$

or —OPO$_3$H$_2$; $d$ is one or two; $m$ is zero or one, $n$ is one or two, except when A is $$-\text{OP}_2\text{H},\overset{\text{O}}{\underset{|}{}}$$

$m$ may be two and when $m$ is zero $d$ is one; and salts thereof said compound containing at least 40 percent by weight of fluorine derived by the R$_f$ portion; and (b) 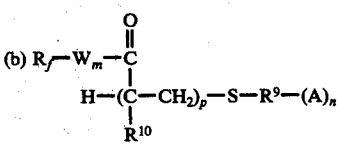

wherein R$_f$, W, A and $n$ are as defined above, R$^9$ is alkyl having 1 to 4 carbon atoms R$^{10}$ is hydrogen or methyl, $p$ is an integer from 2 to 4, inclusive, designating the same or different R$_f$—W groups; and salts thereof, said compound containing at least 40 percent by weight of fluorine derived from the R$_f$ portion;
wherein the ratio of the amine equivalence of said zwitterionic polymer to the acid equivalence of said fluorocarbon is 1/1 to 150/1.

3. Dermally non-irritating solvent-repellent complex formed by mixing together in an aqueous medium a water-soluble zwitterionic polymer selected from the group consisting of
  a. polymers comprising carboxy betaines having the repeating formula $$R^1-\left(\begin{matrix} R^2 \\ | \\ C \\ | \\ R^3 \end{matrix}\right)_x \overset{R^4}{\underset{R^5}{\overset{|}{\underset{|}{\oplus N}}}}-(CH_2)_y-\overset{O}{\overset{\|}{C}}O^{\ominus}$$

wherein $R^1$ is acrylate, methacrylate, acrylamide or methacrylamide; $R^2$ and $R^3$ are hydrogen or alkyl having 1 to 3 carbon atoms; $R^4$ and $R^5$ are hydrogen or alkyl having 1 to 6 carbon atoms; $x$ and $y$ are integers from 1 to 3 inclusive;

b. copolymers comprising monomers (1) and (2) shown below:
 1. substituted acidic vinyl monomers of the formula $$CR^7H=CR^8CO_2H$$

wherein $R^7$ is hydrogen or $$-\overset{O}{\overset{\|}{C}}OH,$$

and $R^8$ is hydrogen, chlorine or —$CH_3$; and 2. substituted basic vinyl monomers having the general formula $$CH_2=CR^6COQ$$

wherein $R^6$ is hydrogen or —$CH_3$—, and Q is an organic radical containing a basic nitrogen-containing group, wherein said acidic and basic functionalities are retained in the copolymer structure and wherein the mole ratio of basic monomer to acidic monomer in said copolymer is from 40/60 to 70/30, except where $R^7$ is $$-\overset{O}{\overset{\|}{C}}OH,$$

the mole ratio is 57/43 to 82/18 with a fluorocarbon compound selected from the group consisting of a. $(R_f)_d$—$(W)_m$—$(A)_n$ wherein $R_f$ is monovalent fluorinated saturated non-aromatic aliphatic radical having 5 to 20 carbon atoms in the skeletal chain; W is a polyvalent linking radical free from functional groups which react with water; A is $$-\overset{O}{\overset{\|}{C}}OH,$$

—$SO_3H$, —$OSO_3H$, $$-OPO_2H \\ \overset{|}{O}$$

or —$OPO_3H_2$; $d$ is one or two; $m$ is zero or one, $n$ is one or two, except when A is $$-OP_2H, \\ \overset{|}{O}$$

$m$ may be two, and when $m$ is zero $d$ is one; and said compound containing at least 40 percent by weight of fluorine derived by the $R_f$ portion; and (b) $R_f$—$W_m$—$\overset{O}{\overset{\|}{C}}$
$\phantom{(b) R_f—W_m—}H-(\overset{|}{\underset{R^{10}}{C}}-CH_2)_p-S-R^9-(A)_n$ wherein $R_f$, W, A and $n$ are as defined above, $R^9$ is alkyl having 1 to 4 carbon atoms, $R^{10}$ is hydrogen or methyl, $p$ is an integer from 2 to 4, inclusive, designating the same or different $R_f$-W groups and said compound containing at least 40 percent by weight of fluorine derived from the $R_f$ portion;

wherein the ratio of the amine equivalence of said zwitterionic polymer to the acid equivalence of said fluorocarbon is 1/1 to 150/1.

4. Complex according to claim 1 wherein Q is —O—$CH_2CH_2$—$NR^{11}$ or —NH—$CH_2CH_2$—$NR_2^{11}$ wherein $R^{11}$ is methyl, ethyl or propyl.

5. Complex according to claim 1 wherein said zwitterionic polymer is a copolymer of the monomers dimethylamino ethyl methacrylate and acrylic acid.

6. Complex according to claim 1 wherein $R_f$ is a perfluoroalkyl radical having 5 to 20 carbon atoms.

7. Complex according to claim 3 wherein $R_f$ is —$C_8F_{17}$.

8. Complex according to claim 1 wherein $m$ is zero and $d$ is one.

9. Complex according to claim 6 wherein the fluorochemical compound is $C_8F_{17}SO_3H$.

10. Complex according to claim 6 wherein the fluorochemical compound is $C_7F_{15}COOH$.

11. Complex according to claim 1 wherein W is selected from the group consisting of $$-SO_2\overset{R^{12}}{\underset{}{\overset{|}{N}}}-(CH_2)_2-O-\overset{O}{\overset{\|}{C}}-(CH_2)_2-S-CH_2-$$

$$-SO_2\overset{R^{12}}{\underset{}{\overset{|}{N}}}-(CH_2)_2-N-\overset{O}{\overset{\|}{C}}-(CH_2)_2-S-CH_2-$$

$$-\overset{O}{\underset{O}{\overset{\uparrow}{\underset{\downarrow}{SO}}}}\!\!-\!\!\bigcirc\!\!-\!\!\underset{R^{13}}{}$$

wherein $R^{12}$ is hydrogen or alkyl having 1 to 4 carbon atoms and $R^{13}$ is hydrogen, $R^{12}$, OH or $OR^{12}$.

12. Complex according to claim 9 wherein W is $$-\overset{O}{\underset{O}{\overset{\uparrow}{\underset{\downarrow}{SO}}}}\!\!-\!\!\bigcirc\!\!-\!\!\underset{R^{12}}{}$$

13. Complex according to claim 1 wherein the fluorochemical compound is the oligomer 14. Complex according to claim 1 wherein A is
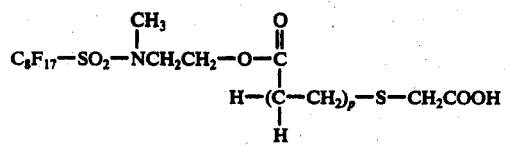
15. Complex according to claim 1 wherein A is
$$-\overset{\overset{\displaystyle O}{\|}}{C}OH.$$
16. Complex according to claim 1 wherein A is
$$-OPO_2H.$$
$$\underset{|}{\overset{O}{\phantom{|}}}$$
16. Complex according to claim 1 wherein the ratio of amine equivalence of said zwitterionic polymer to said fluorocarbon compound is 3/1 to 20/1.
* * * * *

UNITED STATES PATENT AND TRADEMARK OFFICE
CERTIFICATE OF CORRECTION

PATENT NO. : 4,066,589
DATED : January 3, 1978
INVENTOR(S) : NATHANIEL P. LANGFORD AND EDWARD W. PERRAULT It is certified that error appears in the above-identified patent and that said Letters Patent are hereby corrected as shown below:

Col. 24 (claim 3), line 7, change $$\text{"(b)}R_f-W_m-\underset{\underset{R^{10}}{H-(C-CH_2)_p-S-R^9-(A)_n}}{\overset{\overset{O}{\|}}{C}}\text{"}$$

to $$--\text{(b)}R_f-W-\underset{\underset{R^{10}}{H-(C-CH_2)_p-S-R^9-(A)_n}}{\overset{\overset{O}{\|}}{C}}--$$

Signed and Sealed this

Sixth Day of June 1978

[SEAL]

Attest:

RUTH C. MASON
*Attesting Officer*

DONALD W. BANNER
*Commissioner of Patents and Trademarks*